United States Patent [19]

Schmid

[11] Patent Number: 5,052,226
[45] Date of Patent: Oct. 1, 1991

[54] ACCELEROMETER WITH PIEZOELECTRIC ELEMENT

[75] Inventor: Felix Schmid, Belfaux, Switzerland

[73] Assignee: Vibro-Meter SA, Fribourg, Switzerland

[21] Appl. No.: 555,671

[22] Filed: Jul. 18, 1990

Related U.S. Application Data

[63] Continuation of Ser. No. 259,244, Oct. 18, 1988, abandoned.

[30] Foreign Application Priority Data

Nov. 9, 1987 [EP] European Pat. Off. ........... 87810642

[51] Int. Cl.⁵ .................. G01P 15/08; G01M 11/08
[52] U.S. Cl. .................... 73/571 R; 73/654; 310/329
[58] Field of Search .............. 73/517 R, 649, 652, 73/654, 517 A; 310/329

[56] References Cited

U.S. PATENT DOCUMENTS

| 3,400,284 | 9/1968 | Elazor | 73/571 R |
|---|---|---|---|
| 3,893,342 | 7/1975 | Florian et al. | 73/517 R |
| 4,144,747 | 3/1979 | Datwyler, Jr. | 73/862.59 |
| 4,262,544 | 4/1981 | Herzl | 73/861.24 |
| 4,344,010 | 8/1982 | Vig et al. | 310/329 |
| 4,447,755 | 5/1984 | Ghiurea | 73/517 R |
| 4,495,433 | 1/1985 | Sheridan | 73/517 R |
| 4,586,377 | 5/1986 | Schmid | 73/517 R |
| 4,611,490 | 9/1986 | Takeuchi | 73/571 A |
| 4,776,222 | 10/1988 | Lew | 73/861.24 |

FOREIGN PATENT DOCUMENTS

| 2906451 | 7/1980 | Fed. Rep. of Germany . |
|---|---|---|
| 836194 | 6/1960 | United Kingdom . |
| 1601547 | 10/1981 | United Kingdom . |
| 2114301 | 8/1983 | United Kingdom . |

Primary Examiner—John E. Chapman
Attorney, Agent, or Firm—Marks Murase & White

[57] ABSTRACT

The seismic mass is fixed to the mounting base by a tension bolt. This bolt passes with an important play through an opening of the piezoelectric transducer arranged between the mounting base and the seismic mass. Under the influence of inertial forces which act perpendicularly to the axis of the bolt on the seismic mass, bending loads occur which result in an increase of the pressure at one side and in a decrease of the pressure at the other side of the piezoelectric transducer. The transducer has halves polarized in opposite directions and subjected to pressures varying in opposite sense and electrodes covering the top and bottom surfaces of the halves, signals of the same polarity being induced under the bending loads. External influences which act uniformly on the transducer are compensated.

5 Claims, 1 Drawing Sheet

ACCELEROMETER WITH PIEZOELECTRIC ELEMENT

This application is a continuation of application Ser. No. 07/259,244, filed Oct. 18, 1988, now abandoned.

BACKGROUND OF THE INVENTION

The present invention relates to an accelerometer with a seismic mass which exerts intertial forces on at least one electromechanical transducer under the influence of accelerations.

Known accelerometers of this kind comprise between a mounting base and the seismic mass of the accelerometer an element sensitive to pressure, preferably a piezoelectric transducer element. These transducer elements are generally in the form of flat-shaped disks which are polarized in the same direction as the force to be measured. The surface of the electrodes for deriving the charges produced are perpendicular to the direction of polarization, i.e., to the direction of pressure.

Similar accelerometers with transducer elements strained to shear, more particularly piezoelectric elements, are known. In this case, the elements are flat or annular-shaped and they are polarized in parallel with the direction of the force to be measured. The surface of the electrodes which derive the charges produced, are oriented in parallel with the direction of polarization, respectively the direction of shear. In the case of annular elements, the polarization and the direction of the force to be measured is mostly axial.

All known accelerometers use pressure or shear strains which act over the full section of the transducer element. Such transducers are relatively sensitive to external influences, e.g. electric or electromagnetic fields which may induce disturbing signals in the electrodes.

SUMMARY OF THE INVENTION

It is the object of the invention to take measures for reducing such disturbing influences, with the simplest means and high sensitivity of the accelerometer. Embodiments of the invention with their particular advantages will be further described with reference to the drawings.

DETAILED DESCRIPTION OF THE INVENTION

Figure 1:
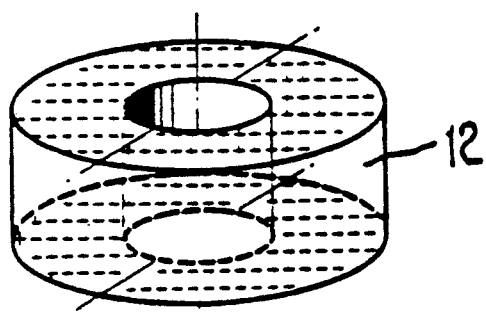
FIG. 1 shows a transducer element with special polarization.
Figure 2:
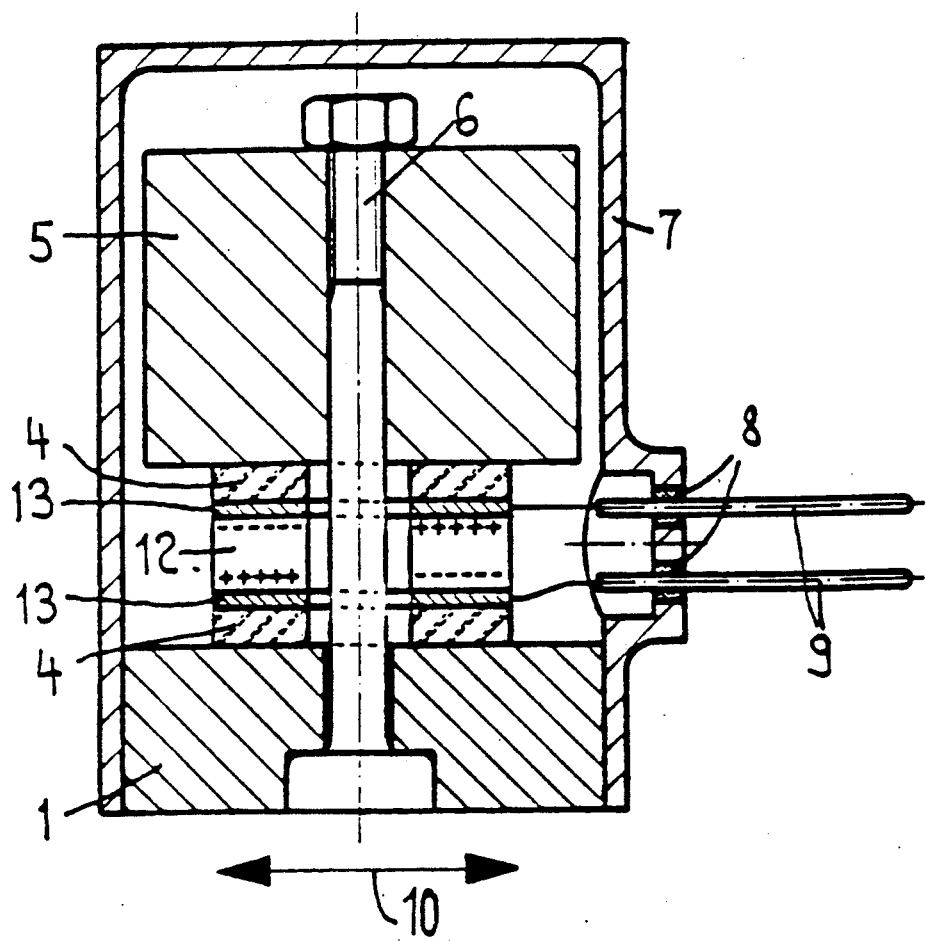
FIG. 2 shows an embodiment with a transducer element according to FIG. 1.

The accelerometer illustrated in FIG. 2 comprises a mounting base 1 and a piezoelectric transducer element 12. The seismic mass 5 is screwed by means of a bolt 6 onto the mounting base 1 and it is pressed against a transducer with such an initial tension that the parts are prestressed and immovably held for all conditions of operation and for each possible orientation of the accelerometer. Through a housing 7, the active mechanical parts are protected and tightly locked. Tight passages 8 for terminal pins 9 are provided in the wall of the housing. Fastening holes (not shown) for the assembly of the accelerometer are provided in the mounting base. The arrow 10 in FIG. 2 shows the axis of sensitivity of the accelerometer. If acceleration occurs in this axis of sensitivity, the inertial forces of the seismic mass 5 produce bending stresses which result in opposite variations of the forces of pressure in the left, respectively the right hand side in the transducer parts illustrated in FIG. 1 or FIG. 2. As an example, an increase of the pressure will take place in the right part of the transducer and a decrease of the pressure will occur in the left part. In this manner, variations of strains will take place which are directed in opposite directions. With other words, the variations of the pressures and of the strains take place in push-pull.

An important novelty with respect to the known embodiments consists however in the use of bending moments instead of using, as known, pure forces of pressure or shear. More particularly in the case of relatively slender constructions of the accelerometer, the gain of charge is more favorable for the same geometrical dimensions than in the usual transducer elements sensitive to shear or pressure, because the bending strains, for an increasing length, increase much more rapidly than the corresponding shear or pressure strains. As can be seen from the preceding, the utilization of bending strains permits, in the simplest manner, loading the transducer in push-pull so that a usual transducer element may be provided simply with a particular electrode arrangement for achieving the mentioned advantages. In the case of pure pressure or shear strains, such a solution would not be possible. It is further possible to increase the sensitivity for constant dimensions of the seismic mass in that one reduces the surface of the cross section of the transducer. Indication has already been made regarding the electrical and geometrical symmetry of the transducer and to the advantages which result thereof. One is namely not only independent of external disturbing influences but also undesired charges are compensated, like the ones which occur due to temperature variations because of the pyroelectric effect. Mechanical strains which are produces by the elongation of the mounting base and/or the housing (called base strain and case strain effects) become largely ineffective because the elongation present in the mounting base or in the housing have approximately the same effect on both halves of the transducer so that the charges produced compensate mutually.

FIGS. 1 and 2 show an embodiment of the present invention. The essential difference consists simply in the arrangement of the electromechanical transducer element 12 of piezoceramics. Contrary to piezocrystals, such ceramics are polarized by applying a strong electric field under determined conditions of temperature, which offers the possibility to polarize different zones of the element in different directions. In the case of the embodiment according to FIGS. 1 and 2, the two halves of the annular transducer element 12 are polarized in opposite directions as shown in FIG. 1. The corresponding polarizations are also indicated in FIG. 2 on the assembled element. In the neutral condition, that is when both halves of the transducer element which are polarized in opposite directions are submitted to equal forces of pressure, equal charges which compensate mutually appear at the upper side and lower side of the element. The transducer is covered in this case with two full annular-shaped electrodes 13 so that in the neutral condition the charges on these electrodes compensate mutually. However, if different forces of pressure act in both halves of the transducer, these forces being due to the inertial forces of the seismic mass 5, variations of charges occur which add up and result in a summation at the terminals 9. As an example, if the pressure increases in the right hand side of FIG. 2, the positive charges at the upper electrode will increase and the negative charge at the lower electrode will decrease. At the same time, the positive charges at the bottom in the left half of the transducer will decrease and the negative charges at the top will increase. This results therefore in a summation of the variations of the charges. In the case of undesired external influences, the compensations mentioned above are again at least partially present. The embodiment according to FIGS. 1 and 2 has the important advantage of an usual, simple electrode arrangement.

I claim:

1. An accelerometer comprising:
   a base;
   a seismic mass;
   a piezo element transducer mounted on said base and coupled to said seismic mass; and
   an output for said transducer;
   said transducer comprising a one piece piezo element having two halves polarized in different directions, said halves being electrically connected therebetween such that seismic influences acting on said seismic mass produce electrical signals on both halves which are added to produce at said output an output signal responsive to said seismic influences.

2. The accelerometer of claim 1 wherein said one piece piezo element has a top face and a bottom face with an electrode mounted on said top face and an electrode mounted on said bottom face.

3. The accelerometer of claim 1, wherein each polarized half has a top face and a bottom face, and further comprising a common electrode mounted on said top faces and a common electrode mounted on said bottom faces so that each electrode contacts both of said polarized halves.

4. The accelerometer of claim 1, further comprising a piezo element having a generally cylindrical configuration having a top circular face, a bottom circular face and an axis extending through the center of said cylindrical configuration and perpendicular to the top and bottom circular faces, wherein said piezo element is polarized axially.

5. The accelerometer of claim 1, wherein said output is connected to a measuring circuit.

* * * * *